(12) United States Patent
Hill et al.

(10) Patent No.: US 6,735,471 B2
(45) Date of Patent: May 11, 2004

(54) METHOD AND SYSTEM FOR ENDOTRACHEAL/ESOPHAGEAL STIMULATION PRIOR TO AND DURING A MEDICAL PROCEDURE

(75) Inventors: Michael R. S. Hill, Minneapolis, MN (US); Scott E. Jahns, Hudson, WI (US); James R. Keogh, Maplewood, MN (US); David E. Euler, Minnetonka, MN (US); Michael R. Ujhelyi, Maple Grove, MN (US); Nancy J. Rakow, Oak Grove, MN (US); Michael A. Colson, Chanhassen, MN (US)

(73) Assignee: Medtronic, Inc., Minneapolis, MN (US)

( * ) Notice: Subject to any disclaimer, the term of this patent is extended or adjusted under 35 U.S.C. 154(b) by 196 days.

(21) Appl. No.: 09/964,308

(22) Filed: Sep. 26, 2001

(65) Prior Publication Data

US 2002/0032468 A1 Mar. 14, 2002

Related U.S. Application Data

(63) Continuation-in-part of application No. 09/670,369, filed on Sep. 26, 2000, which is a continuation-in-part of application No. 09/433,323, filed on Nov. 3, 1999, now Pat. No. 6,266,564, which is a continuation of application No. 09/070,506, filed on Apr. 30, 1998, now Pat. No. 6,006,134, which is a continuation-in-part of application No. 08/640,013, filed on Apr. 30, 1996, now abandoned.

(51) Int. Cl.[7] ............................................... A61N 1/362
(52) U.S. Cl. ............................................... 607/2; 607/3
(58) Field of Search ........................................... 607/2, 3

(56) References Cited

U.S. PATENT DOCUMENTS 4,574,807 A    3/1986    Hewson et al. ........ 128/419 PG
4,671,295 A    6/1987    Abrams et al.
4,722,347 A    2/1988    Abrams et al.
4,753,244 A    6/1988    Landymore et al.
5,014,698 A    5/1991    Cohen
5,024,228 A    6/1991    Goldstone et al.
5,044,367 A    9/1991    Endres et al.
5,056,519 A    10/1991   Vince
5,125,406 A    6/1992    Goldstone et al.
5,127,407 A    7/1992    Tan
5,129,392 A    7/1992    Bardy et al.
5,156,149 A    10/1992   Hudrlik
5,199,428 A    4/1993    Obel et al.
5,203,326 A    4/1993    Collins
5,243,980 A    9/1993    Mehra (List continued on next page.)

FOREIGN PATENT DOCUMENTS

| DE | 28 11 325 | 9/1979 | |
| EP | 0 589 252 A2 | 3/1994 | |
| WO | WO 92/11064 | 7/1992 | |
| WO | WO 97/40885 | 11/1997 | |
| WO | WO 99/07354 | 2/1999 | |
| WO | WO 99/09971 | 3/1999 | |
| WO | WO 99/09973 | 3/1999 | |
| WO | WO 01/00273 | 1/2001 | ............ A61N/1/05 |

*Primary Examiner*—Carl Layno
(74) *Attorney, Agent, or Firm*—Thomas G. Berry; Daniel W. Latham

(57) ABSTRACT

A method of performing a medical procedure, such as surgery, is provided. A nerve is stimulated in order to adjust the beating of the heart to a first condition, such as a stopped or slowed condition. The medical procedure is performed on the heart or another organ. The stimulation of the nerve is stopped in order to adjust the beating of the heart to a second condition, such as a beating condition. The heart itself may also be stimulated to a beating condition, such as by pacing. The stimulation of the nerve may be continued in order to allow the medical procedure to be continued. Systems and devices for performing the medical procedure are also provided.

23 Claims, 9 Drawing Sheets

U.S. PATENT DOCUMENTS

| | | |
|---|---|---|
| 5,265,603 A | 11/1993 | Hudrlik |
| 5,284,146 A | 2/1994 | Czar et al. |
| 5,292,338 A | 3/1994 | Bardy |
| 5,330,507 A | 7/1994 | Schwartz |
| 5,334,221 A | 8/1994 | Bardy |
| 5,354,318 A | 10/1994 | Taepke |
| 5,356,425 A | 10/1994 | Bardy et al. |
| 5,403,356 A | 4/1995 | Hill et al. |
| 5,411,529 A | 5/1995 | Hudrlik |
| 5,417,713 A | 5/1995 | Cohen .................... 607/4 |
| 5,501,703 A | 3/1996 | Holsheimer et al. |
| 5,507,784 A | 4/1996 | Hill et al. |
| 5,540,732 A | 7/1996 | Testerman |
| 5,549,655 A | 8/1996 | Erickson |
| 5,578,061 A | 11/1996 | Stroetmann et al. |
| 5,620,468 A | 4/1997 | Mongeon et al. |
| 5,651,378 A | 7/1997 | Matheny et al. |
| 5,656,420 A | 8/1997 | Chien |
| 5,690,681 A | 11/1997 | Geddes et al. |
| 5,700,282 A | 12/1997 | Zabara |
| 5,792,187 A | 8/1998 | Adams |
| 5,836,994 A | 11/1998 | Bourgeois |
| 5,874,420 A | 2/1999 | Pelleg |
| 5,913,876 A | 6/1999 | Taylor et al. |
| 5,916,239 A | 6/1999 | Geddes et al. |
| 5,964,789 A | 10/1999 | Karsdon |
| 5,995,872 A | 11/1999 | Bourgeois |
| 6,006,134 A | 12/1999 | Hill et al. |
| 6,043,273 A | 3/2000 | Duhaylongsod |
| 6,060,454 A | 5/2000 | Duhaylongsod |
| 6,073,048 A | 6/2000 | Kieval et al. |
| 6,087,394 A | 7/2000 | Duhaylongsod |
| 6,101,412 A | 8/2000 | Duhaylongsod |
| 6,103,722 A | 8/2000 | Schultz et al. |
| 6,127,410 A | 10/2000 | Duhaylongsod |
| 6,141,589 A | 10/2000 | Duhaylongsod |
| 6,253,108 B1 | 6/2001 | Rosborough et al. |
| 6,266,564 B1 | 7/2001 | Hill et al. |
| 6,449,507 B1 * | 9/2002 | Hill et al. ................. 607/9 |

* cited by examiner

METHOD AND SYSTEM FOR ENDOTRACHEAL/ESOPHAGEAL STIMULATION PRIOR TO AND DURING A MEDICAL PROCEDURE

CROSS-REFERENCE TO RELATED APPLICATIONS

This application is a continuation-in-part of application Ser. No. 09/670,369, Sep. 26, 2000, to inventors Hill et al., said application Ser. No. 09/670,369 is a continuation-in-part of application Ser. No. 09/433,323, Nov. 3, 1999, now U.S. Pat. No. 6,266,564 to inventors Hill and Jonkman, said application Ser. No. 09/433,323 is a continuation of application Ser. No. 09/070,506, Apr. 30, 1998, U.S. Pat. No. 6,006,134, to inventors Hill and Jonkman, said application Ser. No. 09/070,506 is a continuation-in-part of application Ser. No. 08/640,013, Apr. 30, 1996, now abandoned.

FIELD OF THE INVENTION

This invention relates to methods for performing a medical procedure, especially a procedure during which it is necessary to adjust the beating of the heart. More particularly, this invention relates to methods and systems of stimulating a nerve in order to modify the beating of a heart to allow a medical procedure to be performed or for blood flow to be controlled.

BACKGROUND OF THE INVENTION

The current leading cause of death in the United States is coronary artery disease in which the coronary arteries are blocked by atherosclerotic plaques or deposits of fat. The typical treatment to relieve a partially or fully blocked coronary artery is coronary artery bypass graph (CABG) surgery.

CABG surgery, also known as "heart bypass" surgery, generally entails using a graph to bypass the coronary obstruction. The procedure is generally lengthy, traumatic and subject to patient risks. Among the risk factors involved is the use of a cardiopulmonary bypass (CPB) circuit, also known as a "heart-lung machine," to pump blood and oxygenate the blood so that the patient's heart may be stopped during the surgery.

Conventional CABG procedures are typically conducted on a stopped heart while the patient is on a (CPB) circuit. A stopped heart and a CPB circuit enables a surgeon to work in a bloodless, still operative field. However, there are a number of problems associated with CABG procedures performed while on CPB including the initiation of a systemic inflammatory response due to interactions of blood elements with the artificial material surfaces of the CPB circuit and global myocardial ischemia due to cardioplegic cardiac arrest. For these reasons, avoiding the use of CPB or cardioplegic cardiac arrest may help minimize post-operative complications.

One method, as disclosed in U.S. Pat. No. 5,651,378 to inventors Matheny and Taylor and in U.S. Pat. No. 5,913,876 to inventors Taylor et al., for facilitating coronary bypass surgery on a beating heart and thereby avoid the use of CPB and cardioplegic cardiac arrest includes stimulating the vagal nerve electrically in order to temporarily stop or substantially reduce the beating of the heart. This may be followed by pacing the heart to start its beating.

Another method, as disclosed in two published PCT applications, WO 99/09971 and WO 99/09973, both to inventor Puskas, involves stopping the beating of the heart during coronary bypass surgery using electrical stimulation of the vagal nerve in combination with administration of drugs. Another method, as disclosed in U.S. Pat. No. 6,060,454 to inventor Duhaylongsod, involves stopping the beating of the heart during coronary bypass surgery via the local delivery of drugs to the heart.

Although it is desirable to stop the heart for a period of time in order to allow the surgeon to accomplish a required task without interference from heart movement, i.e. a motionless operative field, it is undesirable to have the heart stopped for too long a period of time since the body needs, among other things, a constant supply of oxygen. In fact, it is particularly important to maintain sufficient blood flow, and therefore oxygen flow, to the brain. Stopping the heart for prolonged periods of time may cause damage to the patient.

It is thus important to be able to precisely control and coordinate the amount and duration of stimulation to the vagal nerve and the heart. One type of electrode arrangement that allows such precise control is an electrode tube which is suitable for insertion into a patient's trachea or esophagus. This arrangement provides a configuration of electrodes which can not only stimulate a variety of nerve fibers but may also be configured to stimulate the patient's heart, ventilate the patient's lungs and/or control pain during stimulation. This electrode arrangement also allows for sensing or monitoring of various physiological processes.

It would be desirable therefore to provide a method for controllably stopping or slowing the heart intermittently for diagnostic and therapeutic purposes.

Additionally, it would be desirable to provide a method for controllably stopping or slowing the heart intermittently in order to control blood flow.

Additionally, it would be desirable to provide a method for controllably stopping or slowing the heart intermittently in order to perform a medical procedure on the heart or another organ.

Additionally, it would be desirable to provide a means for coordinating stimulation of the heart and other body components.

Additionally, it would be desirable to provide a means for evaluating the stimulation output from a variety of electrodes to determine the best stimulation configuration.

SUMMARY OF THE INVENTION

One aspect of the present invention provides a method for evaluating stimulation during a medical procedure. A site is stimulated with a first electrode arrangement. The stimulation at the site is then evaluated to provide a first stimulation value. The first electrode arrangement may comprise one or more electrodes such as nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes, probe electrodes, cardiac stimulation electrodes, pacing electrodes and epicardial electrodes.

The method may also involve stimulating the site with a subsequent electrode arrangement and evaluating stimulation to provide a subsequent stimulation value. The first stimulation and subsequent stimulation values may be continued with the electrode arrangement associated with the best stimulation value. The subsequent electrode arrangement may comprise one or more electrodes such as nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes, probe electrodes, cardiac stimulation electrodes, pacing electrodes and epicardial electrodes.

Another aspect of the present invention provides a method of performing a medical procedure. A nerve is stimulated with a first electrode arrangement to adjust the beating of a heart to a first condition. Stimulation is evaluated from the first electrode arrangement to provide a first stimulation value. The nerve is then stimulated with a subsequent electrode arrangement and stimulation is evaluated from the subsequent electrode arrangement to provide a subsequent stimulation value. A desired electrode arrangement is selected based on the first stimulation value and the subsequent stimulation value and the nerve is stimulated with the desired electrode arrangement. The first and the subsequent electrode arrangements may comprise one or more electrodes such as nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes, probe electrodes, cardiac stimulation electrodes, pacing electrodes and epicardial electrodes.

The medical procedure may be performed on an organ. Stimulation of the nerve may then be reduced or stopped to adjust the beating of a heart to a second condition. The nerve may then be stimulated a subsequent time to readjust the beating of the heart to the first condition and the medical procedure then continued. The nerve may be stimulated, for example, using transvascular stimulation, endotrachael stimulation, and/or endoesophageal stimulation. The first condition may be a stopped or slowed condition. The second condition may be a beating condition. The heart may be stimulated to adjust the beating of the heart to the second condition. For example, the heart may be stimulated with a first cardiac electrode arrangement to adjust the beating of the heart to the second condition. Stimulation from the first cardiac electrode arrangement may be evaluated to provide a first cardiac stimulation value. The heart may then be stimulated with a subsequent cardiac electrode arrangement and stimulation from this arrangement may then be evaluated to provide a subsequent cardiac stimulation value. A desired cardiac electrode arrangement may then be selected based on the first cardiac stimulation value and the subsequent cardiac stimulation value and the heart may be stimulated with the desired cardiac electrode arrangement. The first and subsequent cardiac electrode arrangements may be one or more electrodes such as nerve stimulation electrodes, cardiac stimulation electrodes, clip electrodes, needle electrodes, probe electrodes, pacing electrodes, patch electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, electrodes, epicardial electrodes, endotracheal electrodes and endoesophageal electrodes.

The method may also include delivering a drug such as a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin, methylxanthine, a $P_2$-purinoceptor agent, an ischemia agent, and a delta opioid agonist may be delivered during the procedure. The drug may be naturally occurring or chemically synthesized.

The nerve may be a nerve such as a vagal nerve, a carotid sinus nerve, a fat pad.

The medical procedure may be surgical procedures, non-surgical procedures, endoscopic procedures, fluoroscopic procedures, stent delivery procedures, aortic aneurysm repairs, cranial aneurysm repairs, delivery of drugs, delivery of biological agents, cardiac surgery with cardiopulmonary bypass circuits, cardiac surgery without cardiopulmonary bypass circuits, brain surgery, cardiograms, heart valve repair, heart valve replacement, MAZE procedures, revascularization procedures, transmyocardial revascularization, percutaneous myocardial revascularization, CABG procedures, anastomosis procedures, beating heart surgery, vascular surgery, neurosurgery, brain surgery, electrophysiology procedures, diagnostic procedures, therapeutic procedures, ablation procedures, ablation of arrhythmias, endovascular procedures, treatment of the liver, treatment of the spleen, treatment of the heart, treatment of the lungs, treatment of major blood vessels, non-invasive procedures, invasive procedures, port-access procedures, imaging procedures, CAT scan procedures, MRI procedures, gene therapy procedures, cellular therapy procedures, cancer therapy procedures, radiation therapy procedures, transplantation procedures, coronary angioplasty procedures, atherectomy procedures and atherosclerotic plaque removal procedures.

Another aspect of the present invention provides a device for performing a medical procedure. The device includes a first electrode arrangement operatively arranged on a stimulation tube and a second electrode arrangement operatively arranged on a stimulation collar. The first and the second electrode arrangements may comprise one or more electrodes such as nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes, probe electrodes, cardiac stimulation electrodes, pacing electrodes and epicardial electrodes. The device may also include a processor for evaluating stimulation from a set of electrodes, the pair of electrodes comprising at least one electrode from the stimulation tube and at least one electrode from the stimulation collar.

Another aspect of the present invention provides a system for performing a medical procedure. The system includes a first electrode arrangement operatively arranged on a stimulation tube and a second electrode arrangement operatively arranged on a stimulation collar, a processor for evaluating stimulation from a set of electrodes, the pair of electrodes comprising at least one electrode from the stimulation tube and at least one electrode from the stimulation collar and a controller for controlling stimulation from the set of electrodes. The first and the second electrode arrangements may comprise one or more electrodes such as nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes, probe electrodes, cardiac stimulation electrodes, pacing electrodes and epicardial electrodes.

The system may also include drug delivery means such as a spray, a cream, an ointment, a medicament, a pill, a patch, a catheter, a cannula, a needle and syringe, a pump, and an iontophoretic drug delivery device for delivering drugs during the medical procedure.

Another aspect of the present invention provides a method of performing heart surgery. A nerve is stimulated with a first electrode arrangement to reduce the beating of a heart. Stimulation from the first electrode arrangement is evaluated to provide a first stimulation value. The nerve is then stimulated with a subsequent electrode arrangement and the stimulation is evaluated to provide a subsequent stimulation value. A desired electrode arrangement is selected based on the first stimulation value and the subsequent stimulation value and the nerve is stimulated with the desired electrode arrangement. The heart is then operated upon. Stimulation of the nerve is then stopped and the heart is stimulated to cause beating of the heart. The nerve is then re-stimulated to re-inhibit beating of the heart and the surgery is continued. The heart may also be stimulated with a first cardiac electrode arrangement to adjust the beating of the heart to the second condition. Stimulation from the first cardiac electrode arrangement may be evaluated to provide a first cardiac stimulation value. The heart may then be stimulated with a subsequent cardiac electrode arrangement and stimulation from this arrangement may be evaluated to provide a subsequent cardiac stimulation value. A desired cardiac electrode arrangement may then be selected based on the first cardiac stimulation value and the subsequent cardiac stimulation value and the heart may be stimulated with the desired cardiac electrode arrangement.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

DETAILED DESCRIPTION OF THE PRESENTLY PREFERRED EMBODIMENTS

Figure 1:
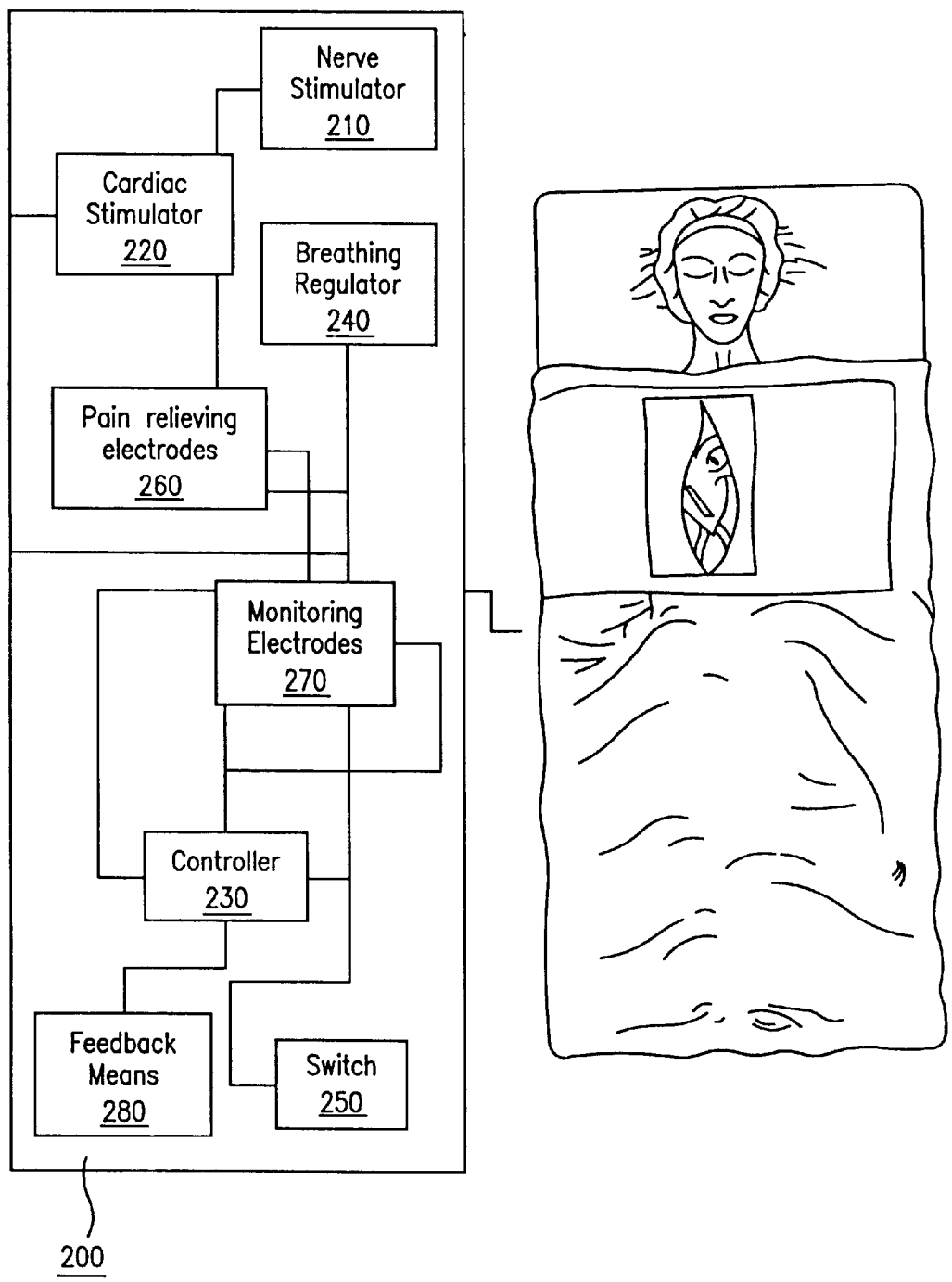
FIG. 1 is a schematic view of one embodiment of a stimulation system in accordance with the present invention.

FIG. 1 shows a schematic view of one embodiment of a stimulation system for performing a medical procedure in accordance with the present invention at 200. Stimulation system 200 may include a nerve stimulator 210, and a cardiac stimulator 220. System 200 may also feature a controller 230 and a breathing regulator 240. System 200 may also feature pain relieving electrodes 260 and monitoring electrodes 270.

In one embodiment, nerve stimulator 210 may be used to electrically manipulate cardiac rhythm by stimulating the vagus nerve. This vagal stimulation may produce asystole (slowing or stopping of the heart's beating.) Once this induced asystole is stopped, i.e. once the vagal stimulation is stopped, the heart may be allowed to return to its usual cardiac rhythm. Alternatively, the heart may be paced with an electrical pacing system, thereby maintaining a normal cardiac output. Vagal stimulation, alone or in combination with electrical pacing, may be used selectively and intermittently to allow a surgeon to perform a medical procedure during intermittent periods of asystole.

It is known that stimulation of the vagus nerve can reduce the sinus rate, as well as prolong AV conduction time or, if stimulation energies are high enough, induce AV node block. Use of vagal nerve stimulation to treat supraventricular arrhythmias and angina pectoris is disclosed in the article "Vagal Tuning" by Bilgutay et al., Journal of Thoracic and Cardiovascular Surgery, Vol. 56, No. 1, July, 1968, pp. 71–82. It is also known that stimulation of the carotid sinus nerve produces a similar result, as disclosed in the article "Carotid Sinus Nerve Stimulation in the Treatment of Angina Pectoris and Supraventricular Tachycardia" by Braunwald et al., published in California Medicine, Vol. 112, pp. 41–50, March, 1970.

As set forth in "Functional Anatomy of the Cardiac Efferent Innervation" by Randall et al., in Neurocardiology, edited by Kulbertus et al, Futura Publishing Co., 1988, direct surgical excision of the fat pad associated with the SA node affects the functioning of the SA node without significantly affecting the AV node. Similarly, excision of the fat pad associated with the AV node affects functioning of the AV node without significantly affecting the SA node.

As set forth in the article "Parasympathetic Postganglionic Pathways to the Sinoatrial Node", Bluemel et al., Am. J. Physiol. 259, (Heart Circ. Physiol. 28) H1504–H1510, 1990, stimulation of the fat pad associated with the SA node results in slowing of the sinus rate without the accompanying prolongation of AV conduction time which normally results from vagal nerve stimulation. The article also indicates that stimulation of the fat pad associated with the AV node is believed to produce corresponding effects limited to the AV node, i.e., extension of the AV conduction time without concurrent slowing of the sinus rate.

As set forth in the article "Neural Effects on Sinus Rate and Atrial Ventricular Conduction Produced by Electrical Stimulation From a Transvenous Electrode Catheter in the Canine Right Pulmonary Artery" by Cooper et al., published in Circulation Research, Vol. 46, No. 1, January, 1980, pp. 48–57, the fat pads associated with both the AV node and the SA node may be stimulated by means of electrodes located in the right pulmonary artery. The results obtained include both a depression of the sinus rate and a prolongation of the AV conduction time in response to continuous stimulation at 2–80 Hz at up to 50 ma.

Generally in healthy individuals, the SA node functions as the pacemaker. Normal heart rhythm associated with the SA node is typically referred to as sinus rhythm. When the SA node fails, the AV node generally takes over creating a heart rate of approximately 35 to 60 beats per minute. Heart rhythm associated with the AV node is typically referred to as nodal rhythm. When the AV node itself is blocked or injured, a new even slower pacemaker site may form at the junction of the AV node and the His bundle. Heart rhythm associated with this junction is typically referred to as junctional escape rhythm. When this junction site is inhibited, the Purkinje fibers in the His bundle or below may act as a pacemaker creating a heart rate of approximately 30 beats per minute. Heart rhythm associated with the Purkinje fibers is typically referred to as idioventricular rhythm.

In one embodiment of the present invention, nerve stimulator 210 may be used to electrically manipulate cardiac rhythm by stimulating the carotid sinus nerve, the fat pad associated with the SA node, the fat pad associated with the AV node, the junction of the AV node and the His bundle and/or the Purkinje fibers.

In one embodiment of the present invention, nerve stimulator 210 may be used alone or in combination with other heart rate inhibiting agents to temporarily stop or slow the beating heart, thereby eliminating or reducing heart motion and/or blood flow during a medical procedure. For example, the present invention may be used to eliminate or reduce motion in the anastomosis field during CABG procedures such that a facilitated anastomosis procedure may be performed safely and effectively. The number of occasions that the vagal nerve may be stimulated depends on the type of medical procedure to be performed. Likewise, the type of medical procedure to be performed will dictate the duration of the individual electrical stimulations.

Nerve stimulator 210 may be powered by AC current, DC current or the may be battery powered either by a disposable or re-chargeable battery. Nerve stimulator 210 may be configured to synchronize activation and deactivation of breathing regulator 240 with vagal stimulation, thereby minimizing or eliminating unwanted heart and chest motion associated with the patient's breathing. Nerve stimulator 210 may be connected to a surgeon controlled switch box. A switch may be incorporated in or on one of the surgeon's instruments, such as surgical site retractor, or any other location easily and quickly accessed by the surgeon for regulation of the nerve stimulator 210 by the surgeon. The switch may be, for example, a hand switch, a foot switch, or a voice-activated switch comprising voice-recognition technologies.

A visual and/or audible signal used to alert a surgeon to the completion or resumption of stimulation may be incorporated into nerve stimulator 210. For example, a beeping tone or flashing light that increases in frequency as the stimulation period should end or begin may be used.

Nerve stimulator 210 may be slaved to cardiac stimulator 220 or cardiac stimulator 220 may be slaved to nerve stimulator 210. For example, the output of cardiac stimulator 220 may be off whenever the output of nerve stimulator 210 is on. Software controlling cardiac stimulator 220 may be designed to automatically commence cardiac pacing if the heart does not resume beating within a pre-determined interval after cessation of vagal nerve stimulation. In addition, the software controlling nerve stimulator 210 may be designed to automatically stop vagal nerve stimulation if the heart has been stopped for too long.

The application of an electrical stimulus to the right or left vagal nerve may include, but is not limited to bipolar and/or monopolar techniques. Nerve stimulation electrodes may be positioned within the body of a patient, positioned on the skin of a patient and/or in combinations thereof. Electrical stimulation may be carried out on the right vagal nerve, the left vagal nerve or to both nerves simultaneously or sequentially. The present invention may include various electrodes, suitable for vagal nerve stimulation to temporarily stop or slow the beating heart alone or in combination with other heart rate inhibiting agents.

Various techniques such as ultrasound, fluoroscopy and echocardiography may be used to facilitate positioning of electrodes. In one embodiment of the present invention, the location of the vagal nerve stimulation electrodes is chosen to elicit maximum bradycardia effectiveness while minimizing current spread to adjacent tissues and vessels and to prevent the induction of post stimulation tachycardia. Furthermore, a non-conductive material such as plastic may be employed to sufficiently enclose the electrodes of all the configurations to shield them from the surrounding tissues and vessels, while exposing their confronting edges and surfaces for positive contact with selected tissues.

Nerve stimulation electrodes of nerve stimulator 210 may be, for example, endotracheal electrodes or esophageal electrodes. Stimulation electrodes may also be electrodes on a sheath or introducer. The sheath or introducer may or may not be splittable. The sheath or introducer may comprise various materials including polymeric materials and metallic materials. The sheath or introducer may be used, for example, with therapeutic or diagnostic catheters. For example, one type of catheter the sheath or introducer may be used with is a venous catheter. The sheath or introducer may comprise one or more electrodes. The electrodes may be arranged, for example, on the surface of the sheath or introducer in a longitudinal pattern or in a circumferential pattern. These electrodes may comprise an electrically conducting material, for example, metal paint, metal tape, metal strips, metal buttons, metal foil, metal wire and/or conductive plastic. The electrodes may be used in a monopolar and/or bipolar arrangement. For example, two electrodes on the sheath or introducer may be used in a bipolar fashion or one electrode on the sheath or introducer may be used in a monopolar fashion in combination with an external skin electrode. The sheath comprising one or more electrodes may be used with a variety of different medical instruments, e.g., catheters, probes, sensors, needles and the like, to provide the stimulation, pacing, pain control and/or sensing capabilities to the instrument.

Nerve stimulation electrodes may also be electrodes on a cannula. The cannula may comprise various materials including polymeric materials and metallic materials. In addition, to stimulation, the cannula may be used, for example, for therapeutic or diagnostic purposes. The cannula may comprise one or more balloons. One or more electrodes may be arranged, for example, on the surface of the cannula in a longitudinal pattern or in a circumferential pattern. The electrodes may also be arranged on one or more balloons attached to the cannula. The electrodes may comprise an electrically conducting material, for example, metal paint, metal tape, metal strips, metal buttons, metal foil, metal wire and/or conductive plastic. The electrodes may be used in a monopolar and/or bipolar arrangement. For example, two electrodes on the cannula may be used in a bipolar fashion or one electrode on the cannula may be used in a monopolar fashion in combination with an external skin electrode.

Figure 2:
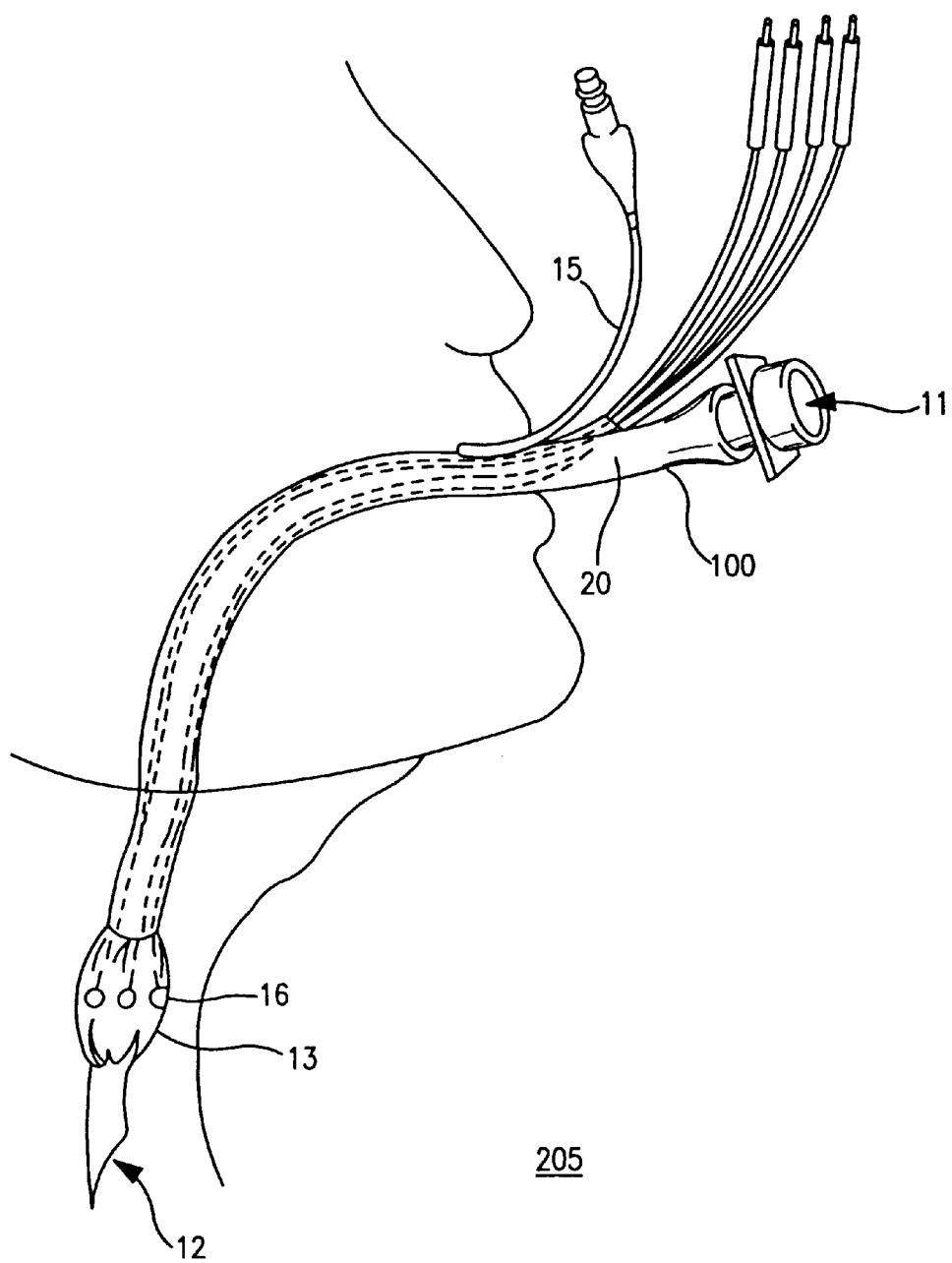
FIG. 2 is a schematic view of one embodiment of an electrode device in accordance with the present invention.

FIG. 2 shows one embodiment of an electrode device comprising endotracheal electrodes in accordance with the present invention at 10A. Electrode device 10A may comprise a tube 100 suitable for insertion through a patient's nose or mouth and into the patient's trachea.

Electrode device 10A may include a first electrode arrangement attached to tube 100. This electrode arrangement may be used to accomplish stimulation on such body components as nerves, muscles, the heart, and the lungs. This stimulation may be used to controllably stop or start an organ such as the heart or lungs or to ease pain. The electrode arrangement may also be used to sense or monitor physiological functions.

Tube 100 may comprise a flexible, non-electrically conducting tube having a proximal end 11 and a distal end 12. Tube 100 may be made of a material selected for its stiffness and flexibility to allow tube 100 to conform readily to the shape of the patient's trachea with minimal trauma to tissue. For example, silicone rubber, polyurethane or other polymers or materials may be used. The outer diameter and length of tube 100 may vary depending upon size of the patient for whom it is intended. Lubricating gels or creams may be used during placement of the device. These lubricating gels or creams may or may not be conductive. Tube 100 may include a biocompatible coating, for example, a slip coating for easier insertion.

Tube 100 may also include main lumen 20 for transporting gases to and from the lungs. Main lumen 20 runs from the proximal end of tube 100 to the distal end of tube 100. Tube 100 may be connected at proximal end 11 to a breathing regulator, which injects and withdraws air from the lungs. Proximal end 11 may include a standard tracheal tube adapter for anesthesia gas connection. Proximal end 11 may include a stop which engages the face of the patient so as to prevent further insertion when the distal end is in the proper location.

An inflatable cuff 13 may be located near distal end 12 of tube 100. Inflatable cuffs are typically used on tracheal tubes to prevent air from escaping by passing between the tube and the trachea wall. Inflatable cuffs may also be used to stabilize the location of electrodes in the trachea. Inflatable cuff 13 is shown in an deflated condition in FIG. 2 and can be inflated by use of a cuff-inflating conduit 15, which may be attached to a source of compressed gas (e.g., air) or fluid (e.g., saline). Cuff-inflating conduit 15 may be a lumen which communicates with the interior of the cuff through a port in the tube. Inflatable cuff 13 may be made of a very soft rubber-like material well known in the catheter art. A check valve may be used to control inflation and deflation of the cuff. Tube 100 may or may not include one or more cuffs. A single inflation lumen in communication with multiple cuffs may be used to inflate the cuffs or each cuff may have its own inflation lumen. Tube 100 may include positioning marks or other positioning technologies.

Associated with tube 100 is an arrangement of electrodes 16. These electrodes may comprise an electrically conducting material, for example, metal paint, metal tape, metal strips, metal buttons, metal foil, metal wire and/or conductive plastic. The electrodes may be ring electrodes, wire electrodes, button electrodes and/or foil electrodes. The electrodes may be used in a monopolar and/or bipolar arrangement. For example, two electrodes on tube 100 may be used in a bipolar fashion or one electrode on tube 100 may be used in a monopolar fashion in combination with an external skin electrode. The electrodes may be arranged parallel to the axis of tube 100 and/or the electrodes may be arranged circumferentially to the axis of tube 100. Tube 100 may comprise one or more electrodes. The electrodes may be located proximal to an inflatable cuff, distal to an inflatable cuff, on one or more inflatable cuffs and/or combinations thereof. For example, in FIG. 2, electrode arrangement 16 comprises an array of electrodes located on the outer surface of inflatable cuff 13. Placement of electrodes on an inflatable cuff may help the electrodes make improved contact with the inner surface of the trachea when the cuff is inflated.

Figure 3:
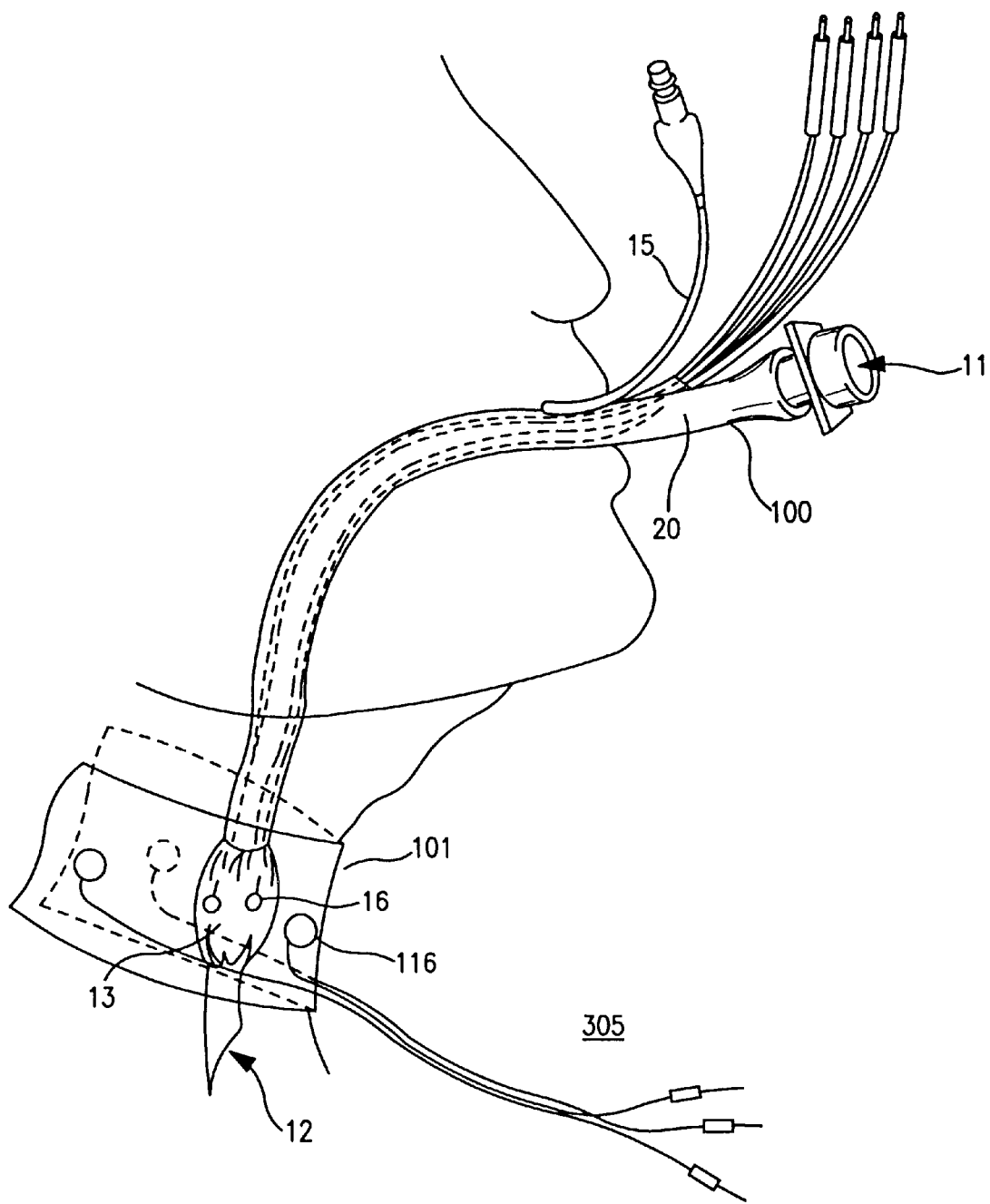
FIG. 3 is a schematic view of one embodiment of an electrode device in accordance with the present invention.

FIG. 3 shows one embodiment of an electrode device comprising endotracheal electrodes in accordance with the present invention at 10B. Electrode device 10B may comprise tube 100, for example, as described above, and a collar 101. Collar 101 may be suitable for external placement on a portion of the body such as, for example, around the neck. Electrode device 10B may include a first electrode arrangement attached to tube 100 and a second electrode arrangement attached to collar 101. These electrode arrangements may be used to accomplish stimulation on such body components as nerves, muscles, the heart, and the lungs. This stimulation may be used to controllably stop or start an organ such as the heart or lungs or to ease pain. The electrodes may also be used to sense or monitor physiological functions.

Collar 101 may comprise a flexible, non-electrically conducting material selected for its stiffness and flexibility to allow collar 101 to conform readily to the shape of the patient's neck. The collar may be adjustable to allow it to fit appropriately the neck size of the patient for whom it is intended. Associated with collar 101 is an arrangement of electrodes 116. These electrodes may comprise an electrically conducting material, for example, metal paint, metal tape, metal strips, metal buttons, metal foil, metal wire and/or conductive plastic. The electrodes may be wire electrodes, button electrodes and/or foil electrodes. The electrodes may be arranged circumferentially around the neck of a patient. Collar 101 may comprise one or more electrodes. Conductive gels or creams may be used in combination with the collar to help improve electrical contact of electrodes 116 with the body of the patient.

Figure 4:
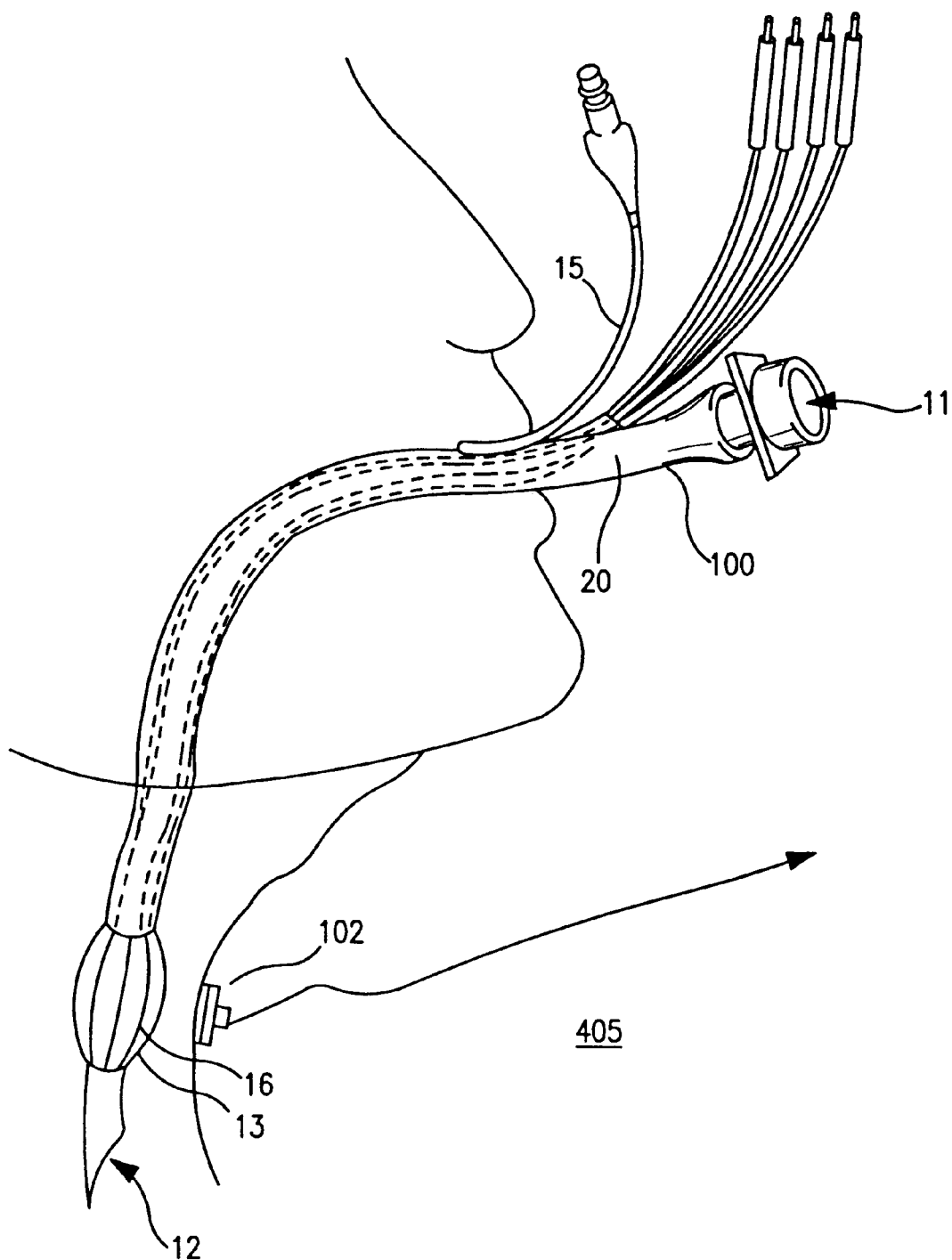
FIG. 4 is a schematic view of one embodiment of an electrode device in accordance with the present invention.

FIG. 4 shows one embodiment of an electrode device comprising endotracheal electrodes in accordance with the present invention at 10C. Electrode device 10C may comprise tube 100, for example, as described above, and one or more external electrodes 102. Electrodes 102 may be suitable for external placement on a portion of the body such as, for example, on the neck or chest. Electrode device 10C may include a first electrode arrangement attached to tube 100 and a second electrode arrangement external to the patient's body, for example external electrode 102. Electrode arrangement 102 may comprise one or more typical external electrodes, for example skin or patch electrodes. The first and second electrode arrangements may be used to accomplish stimulation on such body components as nerves, muscles, the heart, and the lungs. This stimulation may be used to controllably stop or start an organ such as the heart or lungs or to ease pain. The electrodes may also be used to sense or monitor physiological functions.

In FIG. 4, tube 100 is shown comprising an arrangement of metal wire electrodes 16 located on the outer surface of inflatable cuff 13. In this particular embodiment, electrodes 16 are shown as wires that run from a location between the two tube ends 11 and 12 toward distal end 12 in a direction parallel to the tube's central axis. Each electrode wire may have a first portion, located between proximal end 11 and distal end 12, and insulated against electrical contact. Each electrode may also have a second wire portion located on outer surface of cuff 13. Each second wire portion located on outer surface of cuff 13 is uninsulated and capable of forming an electrical contact. This contact may be formed with a body component, such as, for example adjacent muscles or nerves.

Tube 100 comprising at least two electrodes may be used in a bipolar fashion without the use of one or more external electrodes. For example, tube 100 may be used without the use of collar 101 or external electrode 102. Tube 100 comprising one or more electrodes may be used in a monopolar fashion with the use of one or more external electrodes, for example collar 101 or external electrode 102. In addition, electrodes of devices 10A, 10B and 10C, for example, may comprise any means capable of forming electrical contact with, for example, nerve stimulator 210, such as connecting plugs, alligator clips or insulated wires with bared ends.

Figure 5:
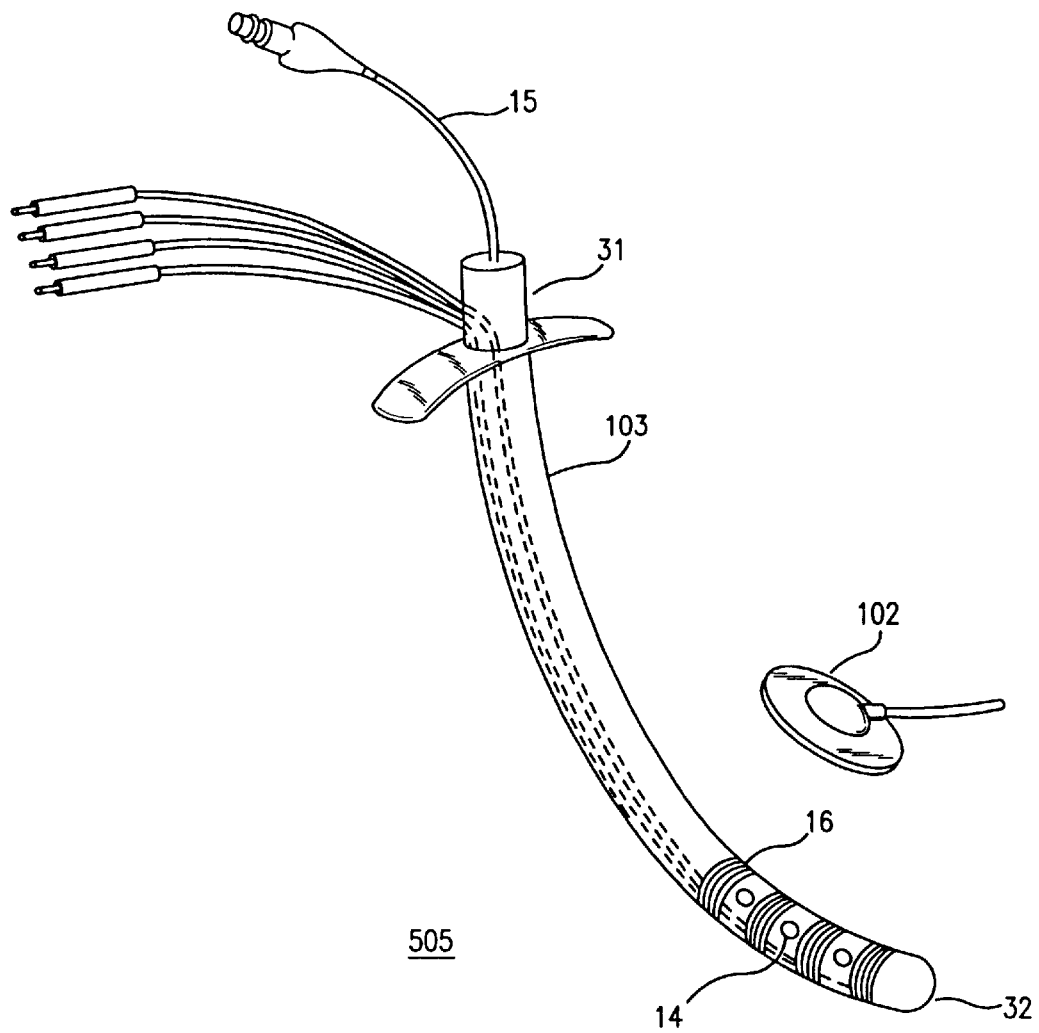
FIG. 5 is a schematic view of one embodiment of an electrode device in accordance with the present invention.

FIG. 5 shows one embodiment of an electrode device comprising esophageal electrodes in accordance with the present invention at 10D. Electrode device 10D may comprise a tube 103 suitable for insertion through a patient's nose or mouth and into the patient's esophagus. Electrode device 10D may comprise one or more external electrodes 102. Electrodes 102 may be suitable for external placement on a portion of the body such as, for example, on the neck or chest. Electrode device 10D may include a first electrode arrangement attached to tube 103 and a second electrode arrangement external to the patient's body, for example external electrode 102. Electrode arrangement 102 may comprise one or more typical external electrodes, for example skin or patch electrodes. The first and second electrode arrangements may be used to accomplish stimulation on such body components as nerves, muscles, the heart, and the lungs. This stimulation may be used to controllably stop or start an organ such as the heart or lungs or to ease pain. The electrodes may also be used to sense or monitor physiological functions.

Tube 103 may comprise a flexible, non-electrically conducting tube having a proximal end 31 and a distal end 32. Tube 103 may be made of a material selected for its stiffness and flexibility to allow tube 103 to conform readily to the shape of the patient's esophagus with minimal trauma to tissue. For example, silicone rubber, polyurethane or other polymers or materials may be used. The outer diameter and length of tube 103 may vary depending upon size of the patient for whom it is intended. Lubricating gels or creams may be used during placement of the device. These lubricating gels or creams may or may not be conductive. Tube 103 may include a biocompatible coating, for example, a slip coating for easier insertion. Tube 103 may include positioning marks or other positioning technologies.

Associated with tube 103 is an arrangement of electrodes 16. These electrodes may comprise an electrically conducting material, for example, metal paint, metal tape, metal strips, metal buttons, metal foil, metal wire and/or conductive plastic. The electrodes may be ring electrodes, wire electrodes, button electrodes and/or foil electrodes. The electrodes may be used in a monopolar and/or bipolar arrangement. For example, two electrodes on tube 103 may be used in a bipolar fashion or one electrode on tube 103 may be used in a monopolar fashion in combination with an external skin electrode 102. The electrodes may be arranged parallel to the axis of tube 103 and/or the electrodes may be arranged circumferentially to the axis of tube 103. Tube 103 may comprise one or more electrodes. The electrodes may be located proximal to an inflatable cuff or hole, distal to an inflatable cuff or hole, on one or more inflatable cuffs and/or combinations thereof. For example, in FIG. 5, electrode arrangement 16 comprises an array of wire electrodes wrapped around the outer surface of tube 103 and arranged around multiple holes 14.

One or more holes 14 in tube 103 in the area of the electrodes 16 provides a means of ensuring better electrical contact with the esophageal wall and electrodes 16 when suction is introduced through suction conduit 18. Suction conduit 18 may be attached to a vacuum source. Suction conduit 18 may be a lumen which communicates with one or more holes 14 through a port in tube 103. A variety of securing means besides holes 14 may be used for improving electrical contact between electrodes and esophageal wall, for example suction pods or a sticky biocompatible substance may be used.

Figure 6:
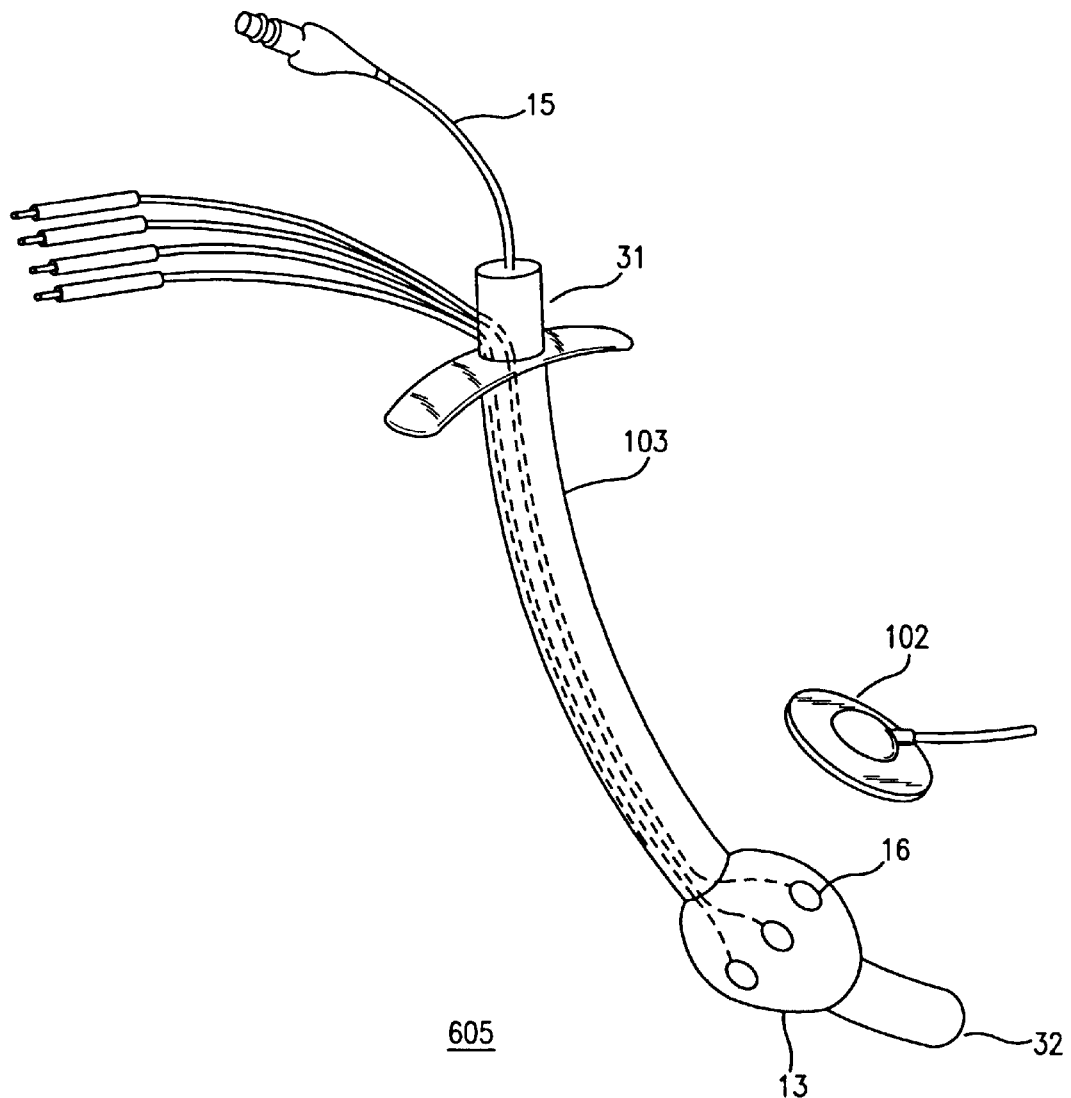
FIG. 6 is a schematic view of one embodiment of an electrode device in accordance with the present invention.

FIG. 6 shows one embodiment of an electrode device comprising esophageal electrodes in accordance with the present invention at 10E. Electrode device 10E may comprise a tube 103 suitable for insertion through a patient's nose or mouth and into the patient's esophagus. Electrode device 10D may comprise one or more external electrodes 102 as described above.

As shown in FIG. 6, an inflatable cuff 13 may be located near distal end 32 of tube 103. Inflatable cuff 13 may be used to stabilize the location of electrodes in the esophagus. Inflatable cuff 13 is shown in an inflated condition in FIG. 5 and can be inflated and deflated by use of a cuff-inflating conduit 15, which may be attached to a source of compressed gas (e.g., air) or fluid (e.g., saline). Cuff-inflating conduit 15 may be a lumen which communicates with the interior of the cuff through a port in the tube. Inflatable cuff 13 may be made of a very soft rubber-like material well known in the catheter art. A check valve may be used to control inflation and deflation of the cuff. Tube 103 may or may not include one or more cuffs. A single inflation lumen in communication with multiple cuffs may be used to inflate the cuffs or each cuff may have its own inflation lumen. Placement of electrodes 16 on inflatable cuff 13 may help the electrodes make improved contact with the inner surface of the esophagus when the cuff is inflated. Tube 103 may include positioning marks or other positioning technologies.

Tube 103 comprising at least two electrodes may be used in a bipolar fashion without the use of one or more external electrodes. For example, tube 103 may be used without the use of external electrode 102. Tube 103 comprising one or more electrodes may be used in a monopolar fashion with the use of one or more external electrodes, for example external electrode 102. In addition, electrodes of devices 10D and 10E, for example, may comprise any means capable of forming electrical contact with, for example, nerve stimulator 210, such as connecting plugs, alligator clips or insulated wires with bared ends.

System 200 may also include cardiac stimulator 220 which may be used to stimulate the heart as desired. As with nerve stimulator 210, cardiac stimulator 220 may be intermittently stopped and started to allow the surgeon to perform individual steps of a medical procedure.

Cardiac stimulator 220 may further comprise a conventional ventricular demand pacer or dual chamber (atrial-ventricular) pacer. Cardiac stimulator 220 may be powered by AC current, DC current or may be battery powered either by a disposable or re-chargeable battery. Cardiac stimulator 220 may be configured to synchronize activation and deactivation of breathing regulator 240 with pacing, thereby minimizing or eliminating unwanted heart and chest motion associated with the patient's breathing. Cardiac stimulator 220 may also comprise any conventional pacing device suitable for ventricular demand pacing.

Cardiac stimulator 220 may be combined in a single unit with a switch box. Cardiac stimulator 220 may comprise a surgeon controlled switch box. A switch may be incorporated in or on one of the surgeon's instruments, such as surgical site retractor, or any other location easily and quickly accessed by the surgeon for regulation of the cardiac stimulator by the surgeon. The switch may be, for example, a hand switch, a foot switch, or a voice-activated switch comprising voice-recognition technologies. A single switch may be used to regulate both cardiac stimulator 220 and nerve stimulator 210.

A visual and/or audible signal used to prepare a surgeon for the resumption of pacing may be incorporated into cardiac stimulator 220. For example, a beeping tone or flashing light that increases in frequency as the pacing period ends may be used. A single signaling method or device may be used for both cardiac stimulator 220 and nerve stimulator 210.

Cardiac stimulator 220 may comprise any type of electrodes suitable for stimulating the heart, for example, non-invasive electrodes, e.g., clips, or invasive electrodes, e.g., needles or probes may be used. Cardiac stimulation electrodes may be positioned through a thoracotomy, sternotomy, endoscopically through a percutaneous port, through a stab wound or puncture, through a small incision in the chest, placed on the chest or in combinations thereof. The present invention may also use various electrodes, catheters and electrode catheters suitable for pacing the heart, e.g., epicardial, endocardial, patch-type, intravascular, balloon-type, basket-type, umbrella-type, tape-type electrodes, suction-type, pacing electrodes, endotracheal electrodes, esophageal electrodes, transcutaneous electrodes, intracutaneous electrodes, screw-type electrodes, barb-type electrodes, bipolar electrodes, monopolar electrodes, metal electrodes, wire electrodes, catheter sheath electrodes, introducer electrodes, cannula electrodes and cuff electrodes. The electrodes may comprise an electrically conducting material, for example, metal paint, metal tape, metal strips, metal buttons, metal foil, metal wire and/or conductive plastic. Guided or steerable catheter devices comprising electrodes may be used alone or in combination with the electrodes.

Cardiac stimulator 220 may be capable of producing specific pacing and stimulation regimes. For example, cardiac stimulator 220 may be capable of sensing and treating electromechanical dissociation (EMD) of the heart as disclosed in U.S. Pat. No. 6,253,108 to inventors Rosborough and Deno and/or cardiac stimulator 220 may be capable of sensing and treating tachyarrhythmia of the heart using specific pacing and/or stimulation regimes. In some patients, EMD and/or tachyarrhythmia may occur during and/or post the medical procedure. The pacing and stimulation regimes may be specific for periods before the procedure, during the procedure and post the procedure. The pacing and stimulation regimes may also be specific for patient recovery, if the patients do not respond following a period of cardiac asystole.

Nerve stimulator 210 and/or cardiac stimulator 220 may be slaved to a robotic system or a robotic system may be slaved to nerve stimulator 210 and/or cardiac stimulator 220. Breathing regulator 240 and other components may also be slaved to such a system. Computer- and voice-controlled robotic systems that position and maneuver endoscopes and/or other surgical instruments for performing microsurgical procedures such as anastomoses through small incisions may be used by a surgeon to perform precise and delicate maneuvers. These robotic systems may allow a surgeon to perform a variety of microsurgical procedures including endoscopic CABG. Endoscopic CABG may allow multiple occluded coronary arteries to be bypassed without a thoracotomy or mini-thoracotomy. Heart valve repair and replacement may also be other surgical applications for these robotic systems. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

System 200 may also include a breathing regulator 240. In one embodiment, the breathing regulator 240 may be used to stimulate the phrenic nerve in order to provide a diaphragmatic pacemaker. Breathing regulator 240 may comprise one or more electrodes for supplying electrical current to the phrenic nerve to control breathing during vagal and/or cardiac stimulation and/or destimulation. Electrodes used to stimulate the phrenic nerve may be, for example, non-invasive, e.g., clips, or invasive, e.g., needles or probes. The application of an electrical stimulus to the phrenic nerve may include, but is not limited to bipolar and/or monopolar techniques. Different electrode positions are accessible through various access openings, for example, in the cervical or thorax regions. Nerve stimulation electrodes may be positioned through a thoracotomy, sternotomy, endoscopically through a percutaneous port, through a stab wound or puncture, through a small incision, placed on the skin or in combinations thereof. The present invention may include various electrodes, catheters and electrode catheters suitable for phrenic nerve stimulation to control breathing.

Phrenic nerve stimulation electrodes may be intravascular, patch-type, balloon-type, basket-type, umbrella-type, tape-type, cuff-type, suction-type, screw-type, barb-type, bipolar, monopolar, metal, wire, endotracheal electrodes, esophageal electrodes, intravascular electrodes, transcutaneous electrodes, catheter sheath electrodes, introducer electrodes, cannula electrodes or intracutaneous electrodes. The electrodes may comprise an electrically conducting material, for example, metal paint, metal tape, metal strips, metal buttons, metal foil, metal wire and/or conductive plastic. Guided or steerable catheter devices comprising electrodes may be used alone or in combination with the nerve stimulation electrodes. For example, a catheter comprising one or more wire, metal strips or metal foil electrodes or electrode arrays may be used. The catheter may comprise, for example, a balloon that may be inflated with air or liquid to press the electrodes firmly against a vessel wall that lays adjacent the phrenic nerve.

Phrenic nerve stimulation electrodes may be oriented in any fashion along a device, including longitudinally or transversely. Various techniques such as ultrasound, fluoroscopy and echocardiography may be used to facilitate positioning of the electrodes. If desired or necessary, avoidance of obstruction of blood flow may be achieved with notched catheter designs or with catheters that incorporate one or more tunnels or passageways.

In another embodiment, the breathing regulator may comprise a connector that interfaces with a patient's respirator, and sends a logic signal to activate or deactivate the respirator to control breathing during vagal and/or cardiac stimulation and/or destimulation.

System 200 may also include electrodes for relieving pain such as indicated at 260. In one embodiment, pain-relieving electrodes may be used to stimulate the spinal cord. Pain relieving electrodes 260 may comprise one or more electrodes for supplying electrical current to control pain during vagal and/or cardiac stimulation and/or destimulation. Electrodes used to relieve pain may be, for example, non-invasive, e.g., clips, or invasive, e.g., needles or probes. The application of an electrical stimulus to relieve pain may include, but is not limited to bipolar and/or monopolar techniques. The electrodes may comprise an electrically conducting material, for example, metal paint, metal tape, metal strips, metal buttons, metal foil, metal wire and/or conductive plastic. Different electrode positions are accessible through various access openings, for example, in the cervical or thorax regions. Nerve stimulation electrodes may be positioned through a thoracotomy, sternotomy, endoscopically through a percutaneous port, through a stab wound or puncture, through a small incision, placed on the skin or in combinations thereof. The present invention may include various electrodes, catheters and electrode catheters suitable for the control of pain.

Pain relieving electrodes 260 may be intravascular, patch-type, balloon-type, basket-type, umbrella-type, tape-type, cuff-type, suction-type, screw-type, barb-type, bipolar, monopolar, metal, wire, endotracheal, endoesophageal, intravascular, transcutaneous or intracutaneous electrodes. Guided or steerable catheter devices comprising electrodes may be used alone or in combination with the nerve stimulation electrodes. For example, a catheter comprising one or more wire, metal strips or metal foil electrodes or electrode arrays may be used. The catheter may comprise, for example, a balloon that may be inflated with air or liquid to press the electrodes firmly against a vessel wall that lays adjacent the nerve or portion of the spine to be stimulated.

Pain relieving electrodes may be oriented in any fashion along the device, including longitudinally or transversely. Various techniques such as ultrasound, fluoroscopy and echocardiography may be used to facilitate positioning of the electrodes. If desired or necessary, avoidance of obstruction of blood flow may be achieved with notched catheter designs or with catheters that incorporate one or more tunnels or passageways.

System 200 may also include sensing electrodes 270 to monitor one or more sites of stimulation. Sensing electrodes may be the same electrodes used for nerve stimulation, cardiac stimulation or pain relieving and/or they may be positioned adjacent one or more of the sites of stimulation described above.

System 200 may also include controller 230. Controller 230 may be used to gather information from nerve stimulator 210 and cardiac stimulator 220. Controller 230 may also be used to control the stimulation levels and stimulation duration of nerve stimulator 210 and cardiac stimulator 220. Controller 230 may also gather and process information from the various components of system 200, in particular sensing electrodes 270. This information may be used to adjust stimulation levels and stimulation times of nerve stimulator 210, cardiac stimulator 220, breathing regulator 240 and/or pain relieving electrodes 260. This adjustment may be based, for example, on data received from monitoring electrodes 270.

System 200 may incorporate one or more switches to facilitate regulation of the various components by the surgeon. One such switch is indicated schematically at 250. The switch may be, for example, a hand switch, a foot switch or a voice-activated switch comprising voice-recognition technologies. The switch may be incorporated on one of the surgeon's instruments, such as surgical site retractor, or any other location easily and quickly accessed by the surgeon.

System 200 may also incorporate means for indicating the status of various components to the surgeon such as feedback means 280. These feedback means may comprise a display, a numerical display, gauges, a monitor display or audio feedback. Feedback means 280 may also comprise one or more visual and/or audible signals used to prepare a surgeon for the start or stop of nerve stimulation and/or cardiac stimulation. Alternatively, the feedback means may be incorporated on one of the surgeon's instruments, such as surgical site retractor, or any other location easily and quickly accessed by the surgeon.

Figure 7:
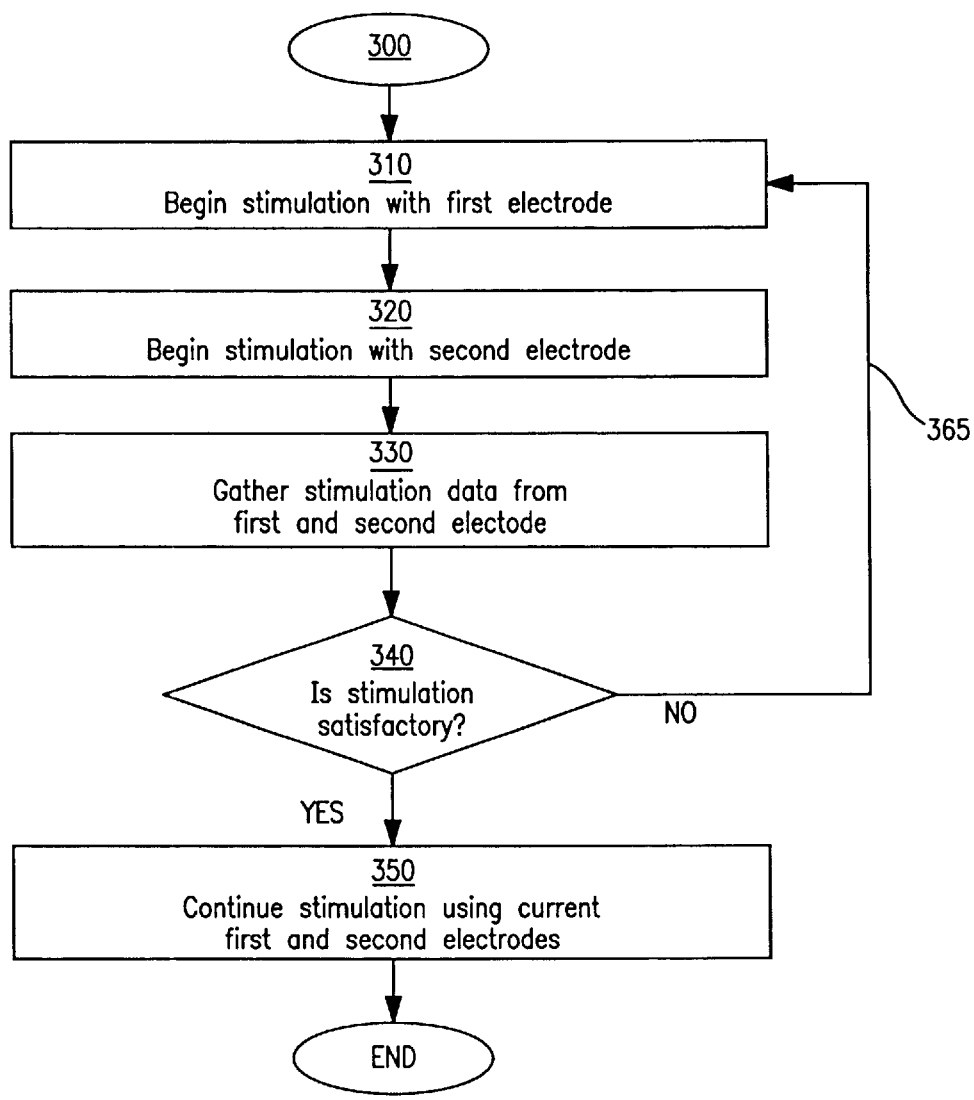
FIG. 7 is a flow diagram of one embodiment of a method of evaluating stimulation during a medical procedure in accordance with the present invention.

FIG. 7 shows a flow diagram of one embodiment of the present invention at 300. Stimulation from at least one electrode of a first electrode arrangement may begin at block 310. In one embodiment of the invention, the first electrode arrangement may be located on tube 100 of device 10. At block 320, stimulation from at least one electrode of a second electrode arrangement is begun. In one embodiment of the invention, the second electrode arrangement may be located on collar 101 of device 10. At block 330, data is gathered regarding the stimulation. For example, data may be gathered from sensing electrodes 270. Alternatively, one or more of the electrodes delivering stimulation may also deliver data to be gathered (i.e. may act as both stimulation and sensing electrodes.) At block 340, the stimulation is evaluated based on the data gathered at block 330. In one embodiment of the invention, the stimulation may be compared to a previously decided value of stimulation. If the stimulation is satisfactory, the stimulation may be continued using the first and second electrode arrangement from blocks 310, 320 (block 350). Alternatively, if the stimulation is not satisfactory, the process may be repeated as designated by loop 365 and another first electrode arrangement is chosen (block 310) followed by another second electrode arrangement (block 320) and further evaluation (blocks 330, 340). This process may repeated until the most satisfactory stimulation is received.

Figure 8:
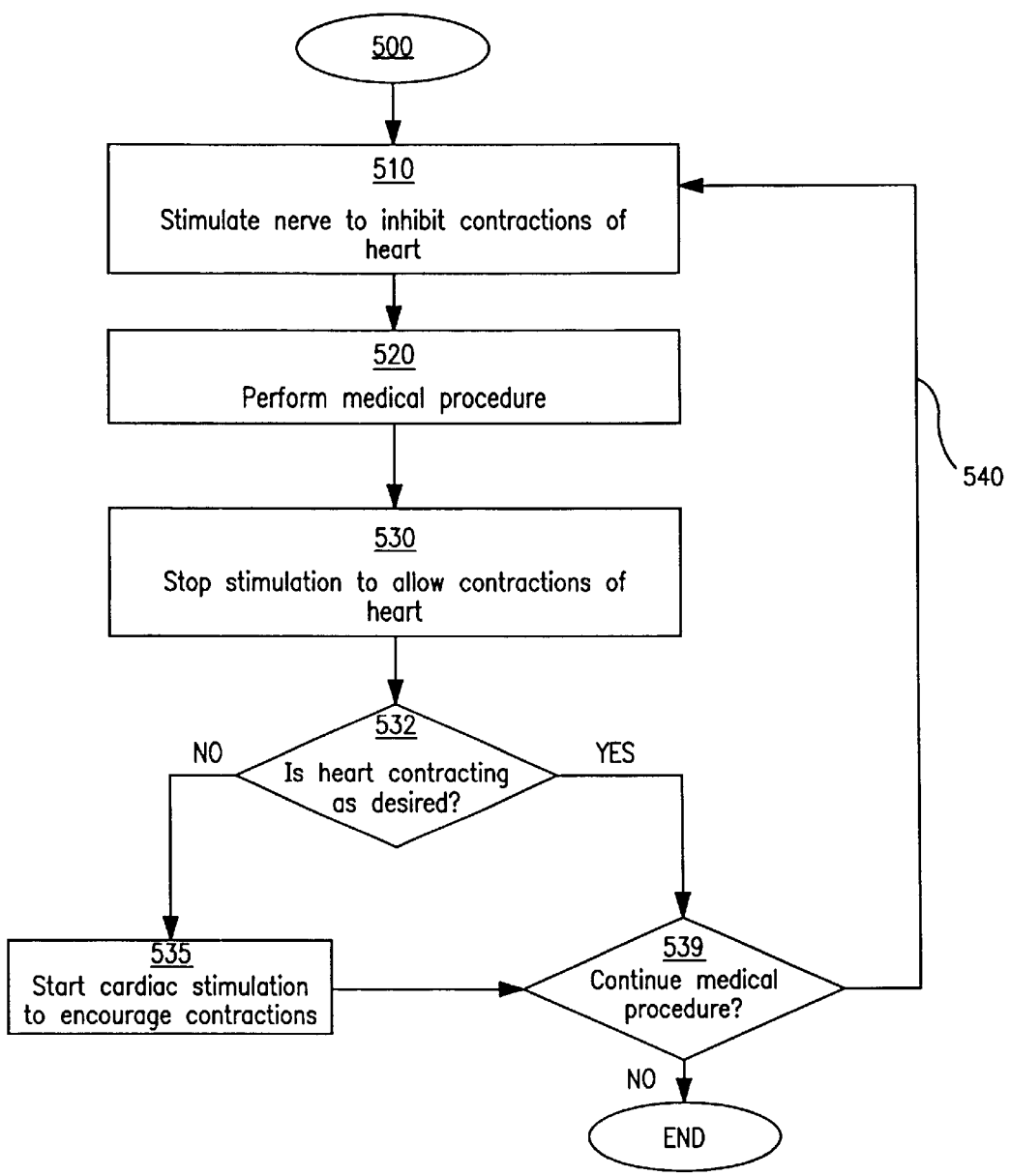
FIG. 8 is a flow diagram of one embodiment of a method of performing a medical procedure in accordance with the present invention.

FIG. 8 shows a flow diagram of one embodiment of the present invention. The patient is prepared for a medical procedure at 500.

At block 510, a nerve that controls the beating of the heart is stimulated. Such a nerve may be for example a vagal nerve. In one embodiment of the invention, at block 510, the routine described in FIG. 3 occurs until the electrode pairing resulting in the most satisfactory stimulation is achieved.

During the procedure 500, one or more of a variety of pharmacological agents or drugs may be delivered (Block 515). These drugs may produce reversible asystole of a heart while maintaining the ability of the heart to be electrically paced. Other drugs may be administered for a variety of functions and purposes as described below. As seen in FIG. 4, drugs delivered at Block 515 may be administered at the beginning of the procedure, intermittently during the procedure, continuously during the procedure, or following the procedure.

Drugs, drug formulations or compositions suitable for administration to a patient during a medical procedure may include a pharmaceutically acceptable carrier or solution in an appropriate dosage. There are a number of pharmaceutically acceptable carriers that may be used for delivery of various drugs, for example, via direct injection, intravenous delivery, intramuscular delivery, oral delivery, topical delivery, hypodermal delivery, suppository delivery, transdermal delivery, epicardial delivery, intraparenteral delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include a oil, sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. Other preservatives include benzalkonium chloride, methyl-paraben, propyl-paraben, and chlorbutanol. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

Drugs may be delivered via a drug delivery device that may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subcdavian or coronary artery. The catheter can be guided into a desired position using various guidance techniques, e.g., flouroscopic guidance and/or a guiding catheter or guide wire techniques.

Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the electrodes may also be used as nerve stimulation electrodes 210 or as cardiac stimulation electrodes 220.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolol, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

Drugs, drug formulations and/or drug compositions that may be used according to this invention may include any naturally occurring or chemically synthesized (synthetic analogues) $P_2$-purinoceptor agents. The term "$P_2$-purinoceptor agent" appearing herein may refer to one or more $P_2$-purinoceptor modulators, mediators, agonists and/or antagonists disclosed in U.S. Pat. No. 5,874,420 to inventor Pelleg. $P_2$-purinoceptors are specific cell surface receptors found on vagal nerve terminals. Vagal tone may be modulated (increased or decreased) by the administration of one or more $P_2$-purinoceptor agents which activate or block these $P_2$-purinoceptor receptors. Examples of $P_2$-purinoceptor agents include, but are not limited to, $P_2$-purinoceptor agonists, $P_2$-purinoceptor antagonists, pyridoxalphosphate-6-azophenyl-2', 4'-disulphonic acid (PPADS), Reactive Blue 2, Cibacron Blue, adenosine 5'-triphosphate (ATP), ATP analogues, capsaicin and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential. The present invention may be combined with conventional CPB, the induced asystole as described by this invention may serve as a substitute for conventional cardioplegic arrest. For example, the combination of drugs and vagal stimulation may be used as a cardioplegic agent in a variety of medical procedures.

Drugs, drug formulations and/or drug compositions that may be used according to this invention may include any naturally occurring or chemically synthesized (synthetic analogues) ischemia agents. The term "ischemia agent" appearing herein may refer to one or more agents that protect one or more organs and/or tissues from ischemic damage. For example, delta opioid receptor modulators, mediators, agonists and/or antagonists as disclosed in U.S. Pat. No. 6,103,722 to inventors Schultz and Gross and in U.S. Pat. No. 5,656,420 to inventor Chien have been used in ischemia protection.

Although it is desirable to stop the heart for a period of time in order to allow the surgeon to accomplish a required task without interference from heart movement, stopping the heart for prolonged periods of time may cause damage to various organs and tissues from ischemia or lack of oxygen. Opioid receptor activation on organs and tissues which possess delta opioid receptors has been shown to elicit a protective effect during periods of ischemia. Delivering an ischemia agent such as a delta opioid agonist to the patient may protect certain organs and tissues such as cardiac and/or brain tissue of the patient from ischemic damage caused by intermittent periods of cardiac asystole. Examples of delta opioid agonists include, but are not limited to, TAN67(−), DPDPE, BW373U86, DADLE, SB219825, SNC80 and SIOM and combinations, mixtures and/or salts thereof.

Drugs, drug formulations and/or drug compositions that may be used during according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics, $P_2$-purinoceptor agents, ischemia agents, delta opioid agonists and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

In one embodiment, the cardiac asystole produced in accordance with the present invention is reversible, e.g., chemically such as by the administration of atropine or by natural forces. Beta-adrenergic stimulation or administration of calcium solutions may be used to reverse the effects of a calcium channel blocker such as verapamil. Agents that promote heart rate and/or contraction may be used in a preferred embodiment of the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

Typically, vagal nerve stimulation prevents the heart from contracting. This non-contraction must then be followed by periods without vagal nerve stimulation during which the heart is allowed to contract.

At Block 520, a medical procedure may be performed or begun. Such a procedure may be for example surgery on the heart. Alternatively, the procedure may be surgery performed on another organ of the body.

The term "medical procedure" may mean any one or more medical or surgical procedures such as, for example cardiac surgery, performed with or without cardiopulmonary bypass (CPB) circuits, heart valve repair, heart valve replacement, MAZE procedures, revascularization procedures, transmyocardial revascularization (TMR) procedures, percutaneous myocardial revascularization (PMR) procedures, CABG procedures, anastomosis procedures, non-surgical procedures, fluoroscopic procedures, beating heart surgery, vascular surgery, neurosurgery, brain surgery, electrophysiology procedures, diagnostic and therapeutic procedures, ablation procedures, ablation of arrhythmias, endovascular procedures, treatment of the liver, spleen, heart, lungs, and major blood vessels, aneurysm repair, imaging procedures of the heart and great vessels, CAT scans or MRI procedures, pharmacological therapies, drug delivery procedures, gene therapies, cellular therapies, cancer therapies, radiation therapies, genetic, cellular, tissue and/or organ manipulation or transplantation procedures, coronary angioplasty procedures, placement or delivery of coated or noncoated stents, atherectomy procedures, atherosclerotic plaque manipulation and/or removal procedures, procedures where bleeding needs to be precisely controlled, procedures that require precise control of cardiac motion and/or bleeding.

When the medical procedure comprises one or more medical devices, e.g., coated stents, these devices may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized.

The medical procedure may be non-invasive, minimally invasive and/or invasive. The medical procedure may entail a port-access approach, a partially or totally endoscopic approach, a sternotomy approach or a thoracotomy approach. The medical procedure may include the use of various mechanical stabilization devices or techniques as well as various robotic or imaging systems.

In one method, the heart may be temporarily slowed or intermittently stopped for short periods of time to permit the surgeon to accomplish the required surgical task and yet still allow the heart itself to supply blood circulation to the body. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers," Dec. 21, 1999, to inventors Hill and Junkman. This patent is assigned to Medtronic, Inc. and is incorporated herein by reference.

After a time, the medical procedure or one phase of the procedure is completed at 520. After some phase of the medical procedure is performed, cardiac contractions are allowed to occur (Block 530) Cardiac contractions may need to occur intermittently during the procedure to ensure adequate blood flow. In one embodiment, the stimulation from the nerve stimulation electrodes is stopped or slowed enough to allow the heart to contract. For example, the vagal nerve stimulation is removed, thereby allowing cardiac contractions to occur.

In another embodiment, the heart may be stimulated to ensure that cardiac contractions occur (Block 535). For example, cardiac stimulation electrodes may be used to apply pacing pulses to the heart to encourage the heart to contract normally. In particular, the pacing pulses may be applied to the ventricle as is well known in the field. In one embodiment of the invention, the routine described in FIG. 3 may take place at this time to evaluate the stimulation from cardiac stimulation electrodes until the most satisfactory pairing of stimulating electrodes is determined.

The present invention permits the heart to be stilled for selected and controllable periods of time in order to permit cardiac or other medical procedure to be performed. While such a period of stillness is desired, it must not last too long, otherwise insufficient blood and oxygen is delivered to organs. Thus, it is necessary to have the periods when the heart is beating (Blocks 530, 535).

If additional medical procedures or additional stages of medical procedures need to be performed, the heart may again be stilled using the methods of stilling the heart described above. Therefore from Block 530 or Block 535, the method may be repeated (Block 540). For example, the heart may again be prevented from contracting by stimulation of the vagal nerve (Block 510). Again, the stimulation electrodes may be evaluated using the routine of the present invention to find the optimal stimulation arrangement. Additional drugs may be delivered or the drugs previously administered may continue to be administered.

Additional surgery, additional steps in the medical procedure or additional medical procedures may again be performed (Block 520) while the heart is still. Then, this stage of stillness may be followed by another stage when the stimulation is removed (Block 530) and the heart is allowed to contract. Again, the heart may be stimulated to encourage contractions (Block 535). Again, the stimulation electrodes may be evaluated using the routine of the present invention to find the optimal stimulation arrangement.

This cycle may be repeated until the procedure, such as the surgery, is completed. After the procedure is completed, step 535 may be performed until the heart is beating normally. At the procedure's end, one or more of a variety of pharmacological agents or drugs may be delivered or may continue to be delivered for example to alleviate pain or aid in recuperation. Other drugs may be administered for a variety of functions and purposes as described above.

For example, a surgical procedure at 520 may require several stitches to be made by the surgeon. The surgeon may stimulate the vagal nerve at 510 to stop the heart. Then the surgeon may make the first stitch at 520. The surgeon may then reduce or halt stimulation at 530 and allow the heart to contract. The surgeon may also pace the heart at 535. Then at 540, the surgeon may return to 510 to inhibit contractions of the heart. At 520, the surgeon will then make the second stitch. This process may be repeated (the loop designated by 540 may be repeated) until all the required stitches have been made.

Figure 9:
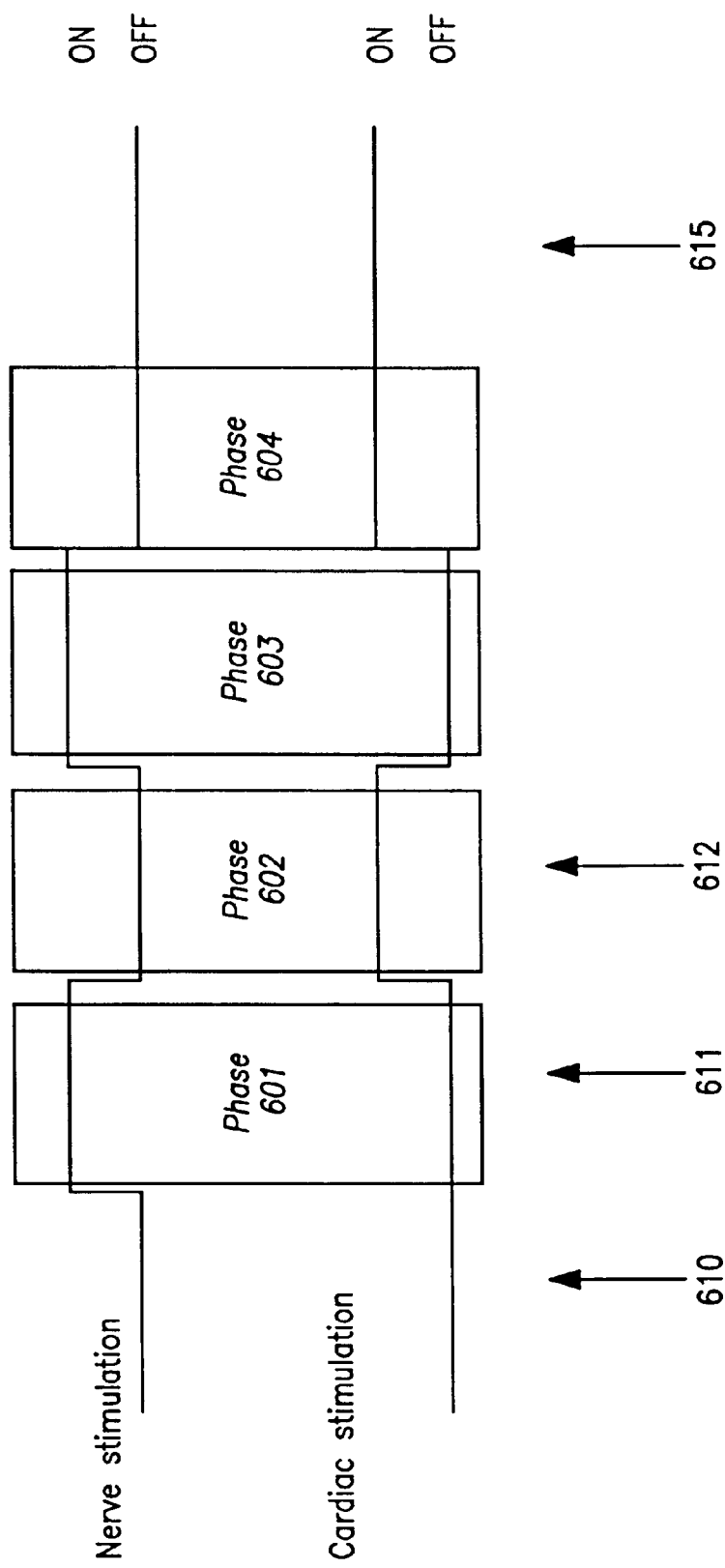
FIG. 9 is a timeline view of one embodiment of a system for controllably stopping or slowing the heart intermittently in a patient during a medical procedure in accordance with the present invention.

FIG. 9 is a timeline showing the relation of the vagal nerve stimulation to the cardiac stimulation in one embodiment of the present invention.

Point 610 indicates a point before the medical procedure has begun. At this point 610, both nerve stimulation and cardiac stimulation are off. At point 610, the heart is beating regularly. Then nerve stimulation is turned on to inhibit beating of the heart. At point 610, the stimulation electrodes used to stimulate the nerve may be evaluated according to the method of the present invention. During phase 601, the vagal nerve stimulation is on and the cardiac stimulation is off. This is the condition of the two types of stimulation at step 520 described above.

Point 611 is a representative point during phase 601. At point 611, the contractions of the heart are stilled or substantially slowed. Then during phase 602 the vagal stimulation is turned off (as described at step 530) and the cardiac stimulation may be turned on (as described at 535). Point 612 is a representative point during phase 602. At point 612, the contractions are allowed and/or may be induced. At point 612, the stimulation electrodes used to stimulation the nerve may be evaluated according to the method of the present invention.

During phase 603, the vagal nerve stimulation is again turned on and the cardiac stimulation is turned off. Then during phase 604 the vagal stimulation is again turned off and the cardiac stimulation may again be turned on. The method of the present invention may be repeated as necessary until a point is reached, represented by point 615, when the necessary medical procedures are completed. At this point 615, nerve stimulation is off although cardiac stimulation may be left on in order to pace the heart to its normal rhythm.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A method of performing a medical procedure, comprising:
   endotracheal stimulation of a vagal nerve to adjust the beating of a heart to a first condition;
   performing the medical procedure on an organ;
   reducing endotracheal stimulation of the vagal nerve;
   epicardial stimulation of the heart to adjust the beating of a heart to a second condition;
   reducing epicardial stimulation of the heart;
   endotracheal stimulation of the nerve a subsequent time in order to re-adjust the beating of the heart to the first condition; and
   continuing the medical procedure.

2. The method of claim 1 wherein the endotracheal stimulation is stopped to achieve the second condition.

3. The method of claim 1 wherein the epicardial stimulation is stopped to re-adjust the beating of the heart to the first condition.

4. The method of claim 1 wherein the first condition is a stopped condition.

5. The method of claim 1 wherein the first condition is a slowed condition.

6. The method of claim 1 wherein the second condition is a beating condition.

7. The method of claim 1 further comprising:
   delivering at least one drug during the medical procedure.

8. The method of claim 7 wherein the drug is selected from the group consisting of:
   a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin, methylxanthine, a $P_2$-purinoceptor agent, an ischemia agent, and a delta opioid agonist.

9. The method of claim 8 wherein the drug is naturally occurring.

10. The method of claim 8 wherein the drug is chemically synthesized.

11. The method of claim 1 wherein the medical procedure is selected from the group consisting of:
    surgical procedures, non-surgical procedures, endoscopic procedures, fluoroscopic procedures, stent delivery procedures, aortic aneurysm repairs, cranial aneurysm repairs, delivery of drugs, delivery of biological agents, cardiac surgery with cardiopulmonary bypass circuits, cardiac surgery without cardiopulmonary bypass circuits, brain surgery, cardiograms, heart valve repair, heart valve replacement, MAZE procedures, transmyocardial revascularization, CABG procedures, beating heart surgery, vascular surgery, neurosurgery, electrophysiology procedures, diagnostic ablation of arrhythmias, therapeutic ablation of arrhythmias, endovascular procedures, treatment of injuries to the liver, treatment of the spleen, treatment of the heart, treatment of the lungs, treatment of major blood vessels, non-invasive procedures, invasive procedures, and port-access procedures.

12. A system for performing a medical procedure, comprising:
    an endotracheal nerve stimulator to inhibit beating of the heart;
    a cardiac stimulator in communication with the endotracheal nerve stimulator to stimulate beating of the heart; and
    a respiratory controller for controlling respiration.

13. The system of claim 12 further comprising:
    drug delivery means for delivering at least one drug during the medical procedure.

14. The system of claim 13 wherein the drug delivery means is selected from the group consisting of:
    a spray, a cream, an ointment, a medicament, a pill, a patch, a catheter, a cannula, a needle and syringe, a pump, and an iontophoretic drug delivery device.

15. The system of claim 14 wherein the endotracheal nerve stimulator stimulates a parasympathetic nerve fiber.

16. The system of claim 15 wherein the endotracheal nerve stimulator stimulates a vagus nerve fiber.

17. The system of claim 12 wherein the endotracheal nerve stimulator comprises at least one electrode.

18. The system of claim 17 wherein the electrode is selected from the group consisting of:
    nerve stimulation electrodes, endotracheal electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes and probe electrodes.

19. The system of claim 12 wherein the cardiac stimulator comprises at least one electrode.

20. The system of claim 19 wherein the electrode is selected from the group consisting of:
    cardiac stimulation electrodes, clip electrodes, needle electrodes, probe electrodes, pacing electrodes, epicardial electrodes, endocardial electrodes, patch electrodes, intravascular electrodes, balloon-type electrodes, basket-type electrodes, tape-type electrodes, umbrella-type electrodes, suction-type electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes.

21. A device for performing a medical procedure comprising:
    a processor;
    an endotracheal nerve stimulation electrode operatively connected to the processor;
    a cardiac stimulation electrode operatively connected to the processor, wherein the processor processes output from the nerve stimulation electrode and adjusts output from the cardiac stimulation electrode based on output from the nerve stimulation electrode; and a drug pump for delivering at least one drug, the drug pump operatively connected to the processor wherein the processor adjusts the output of the drug.

22. A device for performing a medical procedure comprising:

a processor;

an endotracheal nerve stimulation electrode operatively connected to the processor;

a cardiac stimulation electrode operatively connected to the processor, wherein the processor processes output from the nerve stimulation electrode and adjusts output from the cardiac stimulation electrode based on output from the nerve stimulation electrode; and a respiratory controller for controlling respiration, the respiratory controller operatively connected to the processor wherein the processor adjusts the output of the respiratory controller.

23. A device for performing a medical procedure comprising:

a processor;

an endotracheal nerve stimulation electrode operatively connected to the processor and arranged on an endotracheal tube;

a cardiac stimulation electrode operatively connected to the processor, wherein the processor processes output from the nerve stimulation electrode and adjusts output from the cardiac stimulation electrode based on output from the nerve stimulation electrode.

* * * * *